United States Patent [19]
Eichenberger et al.

[11] Patent Number: 6,126,735
[45] Date of Patent: Oct. 3, 2000

[54] PROCESS FOR COLORING HIGH MOLECULAR WEIGHT ORGANIC MATERIAL AND POLYCYCLIC PIGMENTS

[75] Inventors: Thomas Eichenberger, Basel; Max Hügin, Tentlingen, both of Switzerland

[73] Assignee: Ciba Specialty Chemicals Corporation, Tarrytown, N.Y.

[21] Appl. No.: 09/155,733

[22] PCT Filed: Oct. 17, 1997

[86] PCT No.: PCT/EP97/05739

§ 371 Date: Oct. 5, 1998

§ 102(e) Date: Oct. 5, 1998

[87] PCT Pub. No.: WO98/18866

PCT Pub. Date: May 7, 1998

[30] Foreign Application Priority Data

Oct. 25, 1996 [CH] Switzerland .............................. 2634/96

[51] Int. Cl.[7] .......................... C09B 17/00; C09B 57/00; C08K 5/34; C07D 487/14
[52] U.S. Cl. ............................ 106/498; 106/494; 524/89; 544/251
[58] Field of Search ..................... 106/498, 494; 524/89; 544/251

[56] References Cited

U.S. PATENT DOCUMENTS 5,525,152 6/1996 Roschger et al. ...................... 106/498

FOREIGN PATENT DOCUMENTS 4415656 11/1995 Germany .

OTHER PUBLICATIONS

Chem. Abst. 120:772289e of JP 5,202,053[93–202,053] (Aug. 1993).
Patent abst. Of Japan of JP 06–041135 (Feb. 1994).
Derw. Abst. 95–401177/51 of JP 07–278456 (Apr. 1994).
J. of Amer. Chem. Soc. vol. 77 (1955) pp.2243–2248 (No Month).
Ann. 545 (1940) pp. 209–219, Wieland et al. "Uberdie Flugelpigmente der Schmetterlinge" (No Month).
Derw. Abst. 93–290580 of Jp 5202046 (Jan. 1992).
Chemical Abstract No. 121:83370, abstract of Japanese Patent Specification No. 06–041134. Feb. 1994.

Primary Examiner—Anthony Green
Attorney, Agent, or Firm—David R. Crichton

[57] ABSTRACT

A process for mass coloring high molecular weight organic material by using a pyrimidopteridine of formula I and/or II

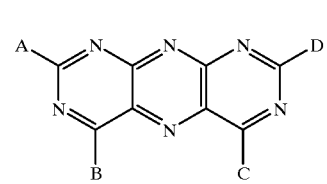

(I)

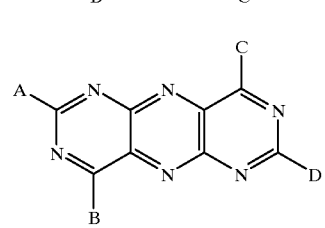

(II)

or a mixture thereof, wherein A, B, C and D are each independently of one another —$NH_2$, —OH, hydrogen, $C_1$–$C_4$-alkyl; phenyl, biphenyl or naphthyl which are unsubstituted or substituted by halogen, —OH, —$NH_2$, $C_1$–$C_4$alkyl or $C_1$–$C_4$alkoxy; —$NHR_1$, —$N(R_1)_2$ or

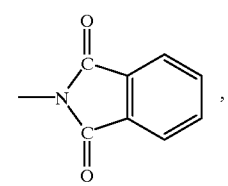

wherein
$R_1$ is $C_1$–$C_4$alkyl; phenyl which is unsubstituted or substituted by halogen, $C_1$–$C_4$alkyl or $C_1$–$C_4$-alkoxy, or —$COXR_2$,
X is a direct bond, —O— or —NH—, and
$R_2$ is $C_1$–$C_4$alkyl; phenyl which is unsubstituted or substituted by halogen, $C_1$–$C_4$alkyl or $C_1$–$C_4$-alkoxy, with the proviso that at least two of the radicals A, B, C and D are —$NH_2$ or —OH.

8 Claims, No Drawings

PROCESS FOR COLORING HIGH MOLECULAR WEIGHT ORGANIC MATERIAL AND POLYCYCLIC PIGMENTS

The present invention relates to a process for mass colouring high molecular weight organic material with pyrimidopteridines as well as to novel pyrimidopteridines.

Pyrimidopteridines are known compounds. In Ann., 545, 209 (1940), H. Wieland et al. mention hydroxy-substituted pyrimidopteridines as reaction products of wing pigments of butterflies. JACS, 77, 2243–2248 (1955), an article devoted to the synthesis of amino- and hydroxy-substituted pyrimidopteridines, describes these products as sparingly soluble yellow substances. Pyrimidopteridines which are substituted at at least two nitrogen atoms of the ring system are disclosed as fluorescent pigments in JP-A 93-202046, JP-A 93-202053, JP-A 94-41135 and JP-A 95-278456. DE-A 4415656 discloses pyrimidopteridine salts as pigments. The known mixtures of pyrimidopteridine compounds with high molecular organic materials normally already have good lightfastness properties which, however, are still not sufficiently good for a number of applications, especially when used as automotive lacquers.

High requirements are placed on pigments which are suitable for a wide range of applications in high molecular weight organic material, such as high chroma, high colour strength, excellent fastness properties, such as fastness to light, weathering, migration and heat, good dispersibility and easy accessibility.

Accordingly, it is the object of this invention to provide a high molecular weight organic material coloured with pyrimidopteridine compounds and having improved fastness to light. In particular, a cumulation of the above-mentioned advantages was to be attained with the pyrimidopteridines which are unsubstituted at the nitrogen atoms of the ring system and which are not saline.

An improved process has accordingly been found for mass colouring high molecular weight organic material with pyrimidopteridines in a manner known per se by using a pyrimidopteridine of formula I and/or II.

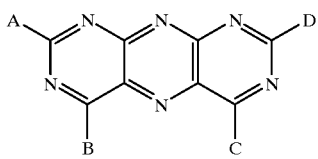

(I)

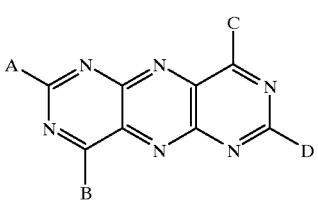

(II)

wherein A, B, C and D are each independently of one another —NH$_2$, —OH, hydrogen, C$_1$–C$_4$-alkyl; phenyl, biphenyl or naphthyl which are unsubstituted or substituted by halogen, —OH, —NH$_2$, C$_1$–C$_4$alkyl or C$_1$–C$_4$alkoxy; —NHR$_1$, —N(R$_1$)$_2$ or

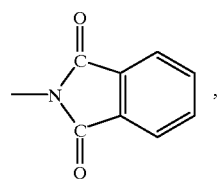

wherein

R$_1$ is C$_1$–C$_4$alkyl; phenyl which is unsubstituted or substituted by halogen, C$_1$–C$_4$alkyl or C$_1$–C$_4$-alkoxy, or —COXR$_2$, X is a direct bond, —O— or —NH—, and R$_2$ is C$_1$–C$_4$alkyl; phenyl which is unsubstituted or substituted by halogen, C$_1$–C$_4$alkyl or C$_1$–C$_4$-alkoxy, with the proviso that at least two of the radicals A, B, C and D are —NH$_2$ or —OH.

The compounds of formulae I and II can also be obtained in another tautomeric form, i.e. those tautomeric forms are also included under formulae I and II.

Should some substituents be halogen, then they are typically fluoro, bromo or chloro, in particular bromo or chloro and, preferably, chloro.

C$_1$–C$_4$Akyl is typically methyl, ethyl, n-propyl, isopropyl, n-butyl, sec-butyl, i-butyl or tert-butyl, and C$_1$–C$_4$alkoxy is typically methoxy, ethoxy, n-propoxy, isopropoxy, n-butoxy, sec-, i- or tert-butoxy.

A special embodiment of this invention relates to a process for colouring high molecular weight organic materials by using pyrimidopteridines of formulae I or II or a mixture thereof, wherein A, B, C and D are each independently of one another —NH$_2$, —OH, hydrogen, methyl, ethyl; phenyl which is unsubstituted or substituted by —OH or —NH$_2$, typically p-hydroxyphenyl and p-aminophenyl, or NHCOXR$_2$, wherein X is a direct bond, —O— or —NH—, and R$_2$ is C$_1$–C$_4$alkyl; phenyl which is unsubstituted or substituted by chloro, methyl, ethyl, methoxy or ethoxy, with the proviso that at least two of the radicals A, B, C and D are —NH$_2$ or —OH.

A particularly preferred embodiment of this invention relates to a process for colouring high molecular weight organic material by using pyrimidopteridines of formula I or II or a mixture thereof, wherein A, B, C and D are each independently of one another —NH$_2$, —OH, hydrogen, methyl; phenyl which is unsubstituted or substituted by —NH$_2$, or —NHCOR$_2$, and R$_2$ is methyl, ethyl or phenyl, and wherein A and D, and B and C, are identical and at least one of the pairs A and D or B and C is —NH$_2$ or —OH.

Particularly preferred pyrimidopteridines of formula I and/or 11 are those, wherein at least one group of A, B, C or D is the radical —NH$_2$. In a particularly preferred embodiment of this invention, at least one of the following pyrimidopteridines is used:

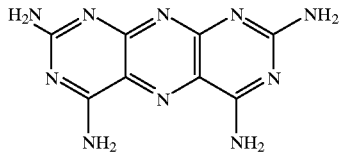

3

-continued

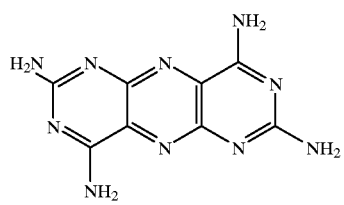

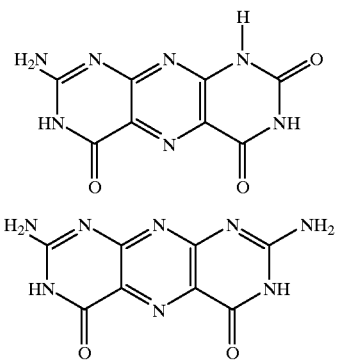

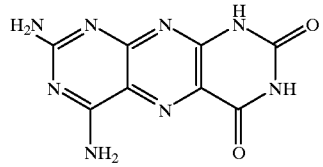

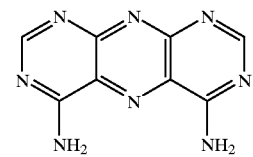

The preparation of the pyrimidopteridines of formulae I and II is usually carried out by methods known per se, such as those described in JACS, 77, 2243–2248 (1955) or in DE-A 4 415 656, for example (I) by oxidative dimerisation of corresponding aminopyrimidines according to the schemes

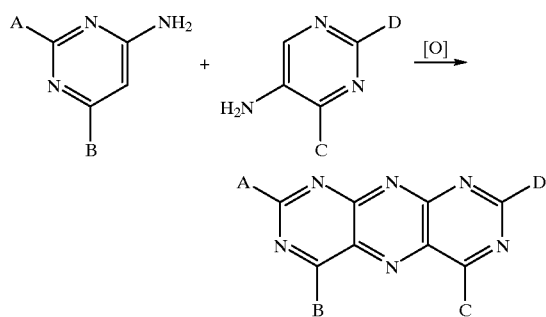

or

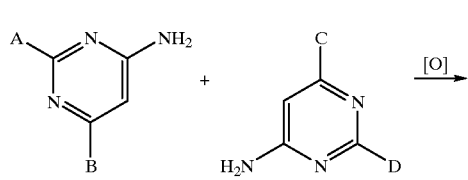

4

-continued

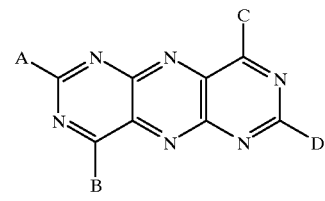

or

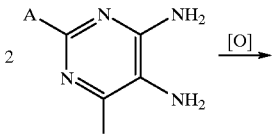

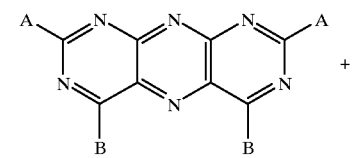

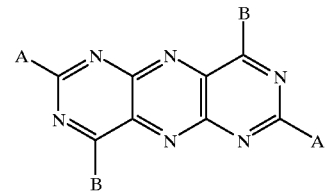

or also by condensation, e.g. according to the schemes

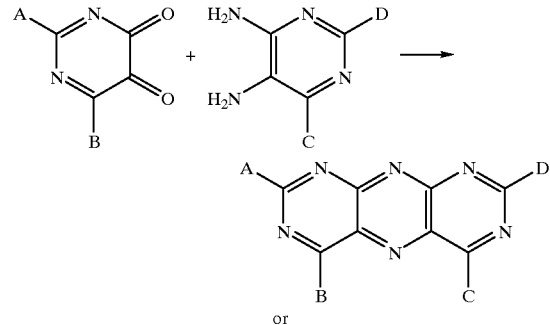

or

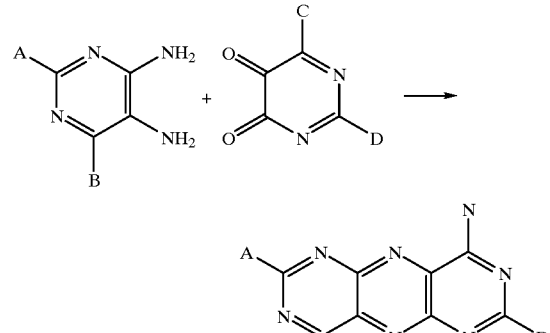

Compounds of formulae I and II, wherein one or two of the radicals A, B, C or D are hydrogen, alkyl substituted aryl, —NHR$_1$ or —N(R$_1$)$_2$, and the others are —OH or —NH$_2$, are novel. Accordingly, this invention also relates to pyrimidopteridines of formula I and/or II wherein one or two of the radicals A, B, C or D are hydrogen, $C_1$–$C_4$alkyl; phenyl, biphenyl or naphthyl which are unsubstituted or substituted by halogen, —OH, —$NH_2$, $C_1$–$C_4$alkyl or $C_1$–$C_4$-alkoxy; —$NHR_1$, —$N(R_1)_2$, or

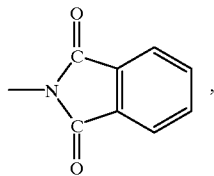, wherein
$R_1$ is $C_1$–$C_4$-alkyl; phenyl which is unsubstituted or substituted by halogen, $C_1$–$C_4$alkyl or $C_1$–$C_4$-alkoxy, or —$COXR_2$,
X is a direct bond, —O— or —NH—, and
$R_2$ is $C_1$–$C_4$alkyl; phenyl which is unsubstituted or substituted by halogen, $C_1$–$C_4$alkyl or $C_1$–$C_4$-alkoxy, and the other radicals A, B, C or D are —OH or —$NH_2$.

Particularly interesting pyrimidopteridines are those of the above structure, wherein one or two of the radicals A, B, C or D are hydrogen, methyl, ethyl; phenyl which is unsubstituted or substituted by —OH or —$NH_2$, or $NHCOXR_2$, wherein
X is a direct bond, —O— or —NH—, and
$R_2$ is $C_1$–$C_4$alkyl, or phenyl which is unsubstituted or substituted by chloro, methyl, ethyl, methoxy or ethoxy, and in particular those, wherein the radicals A and D, and B and C, are identical and either A and D or B and C are —OH or —$NH_2$, the radicals of the other pair being hydrogen, methyl, phenyl which is unsubstituted or substituted by —$NH_2$, or —$NHCOR_2$, and $R_2$ is methyl, ethyl or phenyl.

Illustrative examples of the novel pyrimidopteridines are the following:

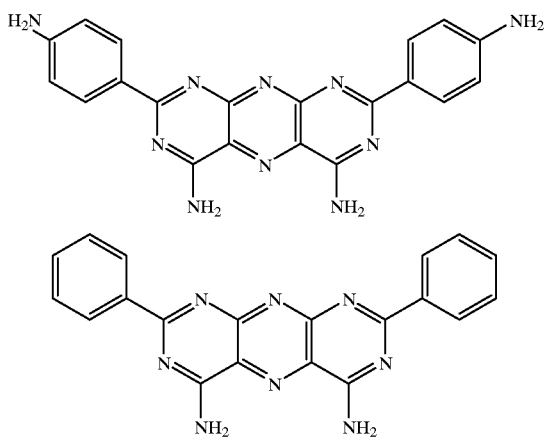

These novel pyrimidopteridines can be prepared in general analogy to the above-mentioned processes. The starting products are usually known substances. Should some of them still be novel they can usually be obtained in general analogy to commonly known methods.

Depending on their substituents and on the polymer to be coloured, the pyrimidopteridines of formulae I and II may be used in the form of polymer-soluble chromophores or, preferably, in the form of pigments. In the latter case it is advantageous to convert the products obtained from the synthesis to a finely dispersed form. This may be effected in different manner, for example:

a) by grinding or kneading, conveniently in the presence of grinding assistants, such as inorganic or organic salts with or without the addition of organic solvents. After grinding, the assistants are removed in customary manner; soluble inorganic salts e.g. with water, and water-insoluble organic solvents e.g. by steam distillation, b) by precipitation from sulfuric acid, methanesulfonic acid, trichloroacetic acid or polyphosphoric acid, c) by converting the crude pigment into an alkali metal salt or amine salt and by hydrolysing the latter. This is effected, for example, by mixing the crude pigment with a base, typically with an alkali metal hydroxide or alkali metal alcoholate, ammonia or amine, in a polar organic solvent, such as dimethylformamide, whereupon the pigment dissolves completely or partially. The pigment is precipitated by hydrolysis, preferably by acidifying the solution which may have been filtered.

It may be found to be convenient to aftertreat the crude pigments or the pigments treated according to a), b) or c) with organic solvents, preferably with solvents that boil at above 100° C.

Particularly suitable for use are benzenes substituted by halogen atoms, alkyl groups or nitro groups, such as xylenes, chlorobenzene, o-dichlorobenzene or nitrobenzene, and pyridine bases, such as pyridine, picoline or quinoline, and also ketones, such as cyclohexanone, ethers, such as ethylene glycol monomethyl ether or ethylene glycol monoethyl ether, amides, such as dimethylformamide or N-methylpyrrolidone as well as dimethylsulfoxide, sulfolane or water by itself, if required under pressure. It is also possible to carry out the aftertreatment in water in the presence of organic solvents and/or with addition of surface-active substances or liquid ammonia or aliphatic amines.

The pigments preferably have a BET surface of 5–150 $m^2/g$. Pigments having a BET surface of 5–30 $m^2/g$ usually tend to have an opaque character whereas those having BET surfaces of 30–150 $m^2/g$ usually tend to be transparent. The BET surface and the particle-size distribution can normally be controlled by the above aftertreatments.

Depending on the envisaged end use it is advantageous to use the pigments as toners or in the form of formulations.

The high molecular weight organic material to be coloured can be of natural or synthetic origin. It may be, for example, natural resins or drying oils, rubber or casein or modified natural substances, such as chlorinated rubber, oil-modified alkyd resins, viscose, cellulose ethers or esters, such as cellulose acetate, cellulose propionate, cellulose acetobutyrate or nitrocellulose and, preferably, synthetic organic polymers (thermosets as well as thermoplastics) such as are obtained by polymerisation, polycondensation or polyaddition. Compounds to be mentioned from the class of the polymerisation resins are, in particular, polyolefins, such as polyethylene, polypropylene or polyisobutylene, and substituted polyolefins, such as polymers from vinyl chloride, vinyl acetate, styrene, acrylonitrile of the acrylate and/or methacrylate or butadiene and also copolymers of the mentioned monomers, in particular ABS or EVA.

Compounds to be mentioned from the series of the polyaddition resins and polycondensation resins are the condensation products of formaldehyde with phenols, the so-called phenolic plastics, and the condensation products of formaldehyde with urea, thiourea and melamine, the so-called amino plastics, the polyesters used as surface coating resins, including the saturated ones, such as alkyd resins, as well as the unsaturated ones, such as maleinate resins, and also the linear polyesters and polyamides or silicones.

The mentioned high molecular weight compounds can be obtained singly or in admixture, as plastic masses or melts which, if desired, may be spun to fibres.

These compounds can also be obtained in the form of their monomers or in polymerised state in dissolved form as film formers or binders for varnishes or printing inks, such as boiled linseed oil, nitrocellulose, alkyd resins, melamine resins, urea/formaldehyde resins or acrylic resins.

The pigmenting of the high molecular weight organic materials with the pigments of formulae and II is typically effected by incorporating such a pigment by itself or in the form of master-batches in these substrates using roll mills, mixing or milling apparatus. The pigmented material is then brought into the desired final form by methods which are known per se, conveniently by calendering, moulding, extruding, coating, casting or by injection moulding. It is often desirable to incorporate plasticisers into the high molecular weight compounds before processing in order to produce non-brittle mouldings or to diminish their brittleness. Suitable plasticisers are typically esters of phosphoric acid, phthalic acid or sebacic acid. In the novel process, the plasticisers may be incorporated before or after working the pigments into the polymers. To obtain different shades, it is also possible to add to the high molecular weight organic materials fillers or other chromophoric components such as white, coloured or black pigments in any amount, in addition to the pyrimidopteridines of formulae I and II.

For pigmenting paints and printing inks, the high molecular weight organic materials and the pyrimidopteridines of formulae I and II, together with optional additives such as fillers, other pigments, siccatives or plasticisers, are finely dispersed or dissolved in a common organic solvent or solvent mixture. The procedure may be such that the individual components by themselves, or also several jointly, are dispersed or dissolved in the solvent and thereafter all the components are mixed.

The colorations so obtained, e.g. in plastic materials, fibres, paint systems or prints, are distinguished by a yellow to red shade, superior colour strength, high chroma, good dispersibility, good fastness to re-coating, migration, heat, light and weathering as well as by good gloss and good IR remission behaviour.

Accordingly, another embodiment of this invention also relates to a mass coloured high molecular weight organic material, which comprises a pyrimidopteridine of formula I and/or II and, preferably, to a mass coloured high molecular weight organic material, which comprises a pyrimidopteridine of formula I and/or II, which material comprises (a) 0.05 to 20% by weight of pyrimidopteridines I and/or II, based on the sum of (a) and (b), and (b) 99.95 to 80% by weight of a high molecular weight organic material, based on the sum of (a) and (b) and, (c) if desired, additives.

Accordingly, another embodiment of this invention relates to the use of the pyrimidopteridines of formulae I and/or II for mass colouring high molecular weight organic material in a manner known per se.

If the pyrimidopteridines of formulae I and II are obtained dissolved in the polymers used, then they are also distinguished by having a pure shade, high colour strength, high fastness to light and also high fluorescence. They are suitable for use in solar energy collectors and for the production of laser radiation.

The following Examples illustrate the invention in more detail.

EXAMPLE 1

198.8 g of commercial 90% 2,4,5,6-tetraaminopyrimidine sulfate are made into a slurry in 1 l of deionised water and this suspension is adjusted to pH 7.9 by addition of 30% aqueous sodium hydroxide solution (measured with a pH glass electrode). At the start of the oxidation process the pH is kept at 7.9, 30% sodium hydroxide solution being added if necessary. The reaction mixture is first stirred for 15 minutes at room temperature and is then heated to 55° C. over 30 minutes. A moderate stream of air is then blown through a tube below surface into the by then almost clear orange solution and the temperature is raised to 85° C. over another 30 minutes. The increasingly thickening orange suspension is then stirred for another 20 hours at 85° C. while blowing in air. After 3 hours, 150 ml of water are added, the pH control is terminated (total consumption of 30% sodium hydroxide solution: 197 ml). The fine orange precipitate is isolated by filtration over a hard filter paper while still hot and the filter cake is washed with 2 l of water. The still moist filter cake is made into a slurry in 10 l of glacial acetic acid and the reaction mixture is stirred for 90 min at 151° C. and filtered over a hard filter paper while still hot. The yellow residue obtained, which still contains some acetic acid, is stirred in 5 l of water and the suspension is adjusted to pH 7 with sodium hydroxide solution and stirred for 15 hours at 95° C. The suspension is filtered over a hard filter paper while still hot and the filter cake is washed with 1.5 l of water. The still moist filter cake is recrystallised in 700 ml of boiling dimethylacetamide for 18 hours (first distilling off some solvent/water mixture until the boiling temperature is 140° C.). The reaction product is filtered hot over a hard filter paper, washed with 250 ml of dimethylacetamide, 300 ml of methanol and 500 ml of water and is then dried, giving 36.07 g (47% of theory) of a yellow powder of formula III

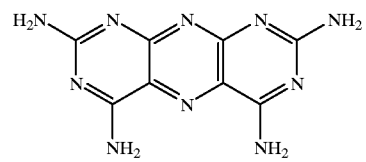

Elemental compostion:        38.79% C,    3.49% H,    56.15% N
(calculated for $C_8H_8N_{10} \cdot 0.25H_2O$:   38.63% C    3.44% H    56.31% N)

EXAMPLE 2

The filtrate mentioned in Example 1, which consists of 10 l of still warm glacial acetic acid, is stood overnight at room temperature. The resultant fine precipitate is isolated by filtration over a hard filter paper and the orange-red residue is stirred in 600 ml of water. The suspension, which has a pH of 4.37, is adjusted to pH 7 with 30% sodium hydroxide solution and is then heated to 90° C. and adjusted once more to pH 7 by further addition of sodium hydroxide solution. The suspension is stirred for one hour at 90° C. and is then filtered hot over a hard filter paper and the filter cake washed with 1200 ml of water. While still moist, the orange-red filter cake is made into a slurry in 600 ml of dimethylacetamide and is heated to boiling temperature, at first distilling off solvent/water mixture until the temperature of the suspension reaches 140° C. The suspension is recrystallised for 17 hours at 140° C. and the reaction product is cooled to 90° C., filtered over a hard filter paper and washed first with 600 ml of methanol and then with 1 l of water and is then dried, giving 1.96 g (2.5% of theory) of an orange-red powder of formula (IV)

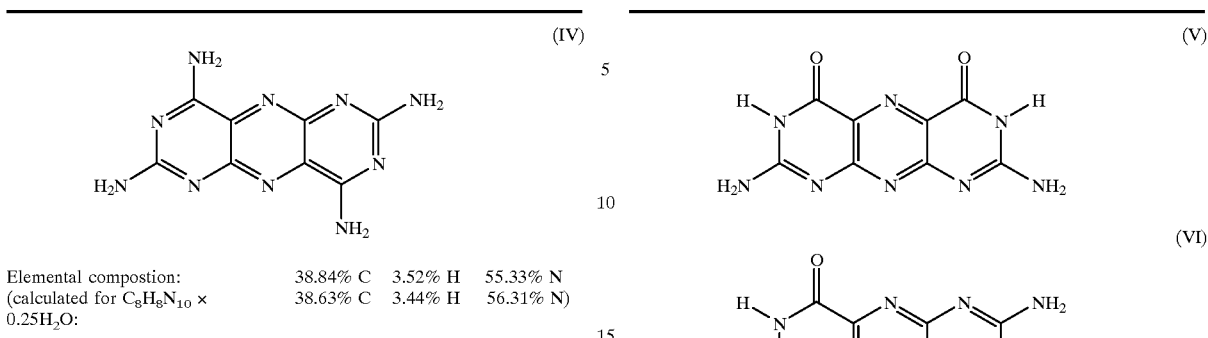

| Elemental compostion: | 38.84% C | 3.52% H | 55.33% N |
|---|---|---|---|
| (calculated for $C_8H_8N_{10}$ × 0.25$H_2O$): | 38.63% C | 3.44% H | 56.31% N) |

EXAMPLE 3

24.66 g of commercial 97% 6-hydroxy-2,4,5-triaminopyrimidinesulfate are made into a slurry in 450 ml of deionised water and the suspension is adjusted to pH 7.5 by adding 30% aqueous sodium hydroxide solution (measured with a pH glass electrode). The reaction mixture is heated to 80° C. over 30 minutes, the pH being continually adjusted to 7.5 by addition of sodium hydroxide solution. A moderate stream of air is then blown into the brownish yellow suspension through a tube below surface, the temperature always being kept at 80° C. After 22 hours, the stream of air is stopped, the orange suspension is cooled to 60° C. and filtered over a hard filter paper. After washing with 150 ml water, the still moist filter cake is mixed with 300 ml of glacial acetic acid (laboratory mixer) and this suspension is placed in a Soxhlet tube and extracted with a further 1200 ml of boiling glacial acetic acid over 2 hours. The orange residue is collected by suction from the Soxhlet tube on a hard filter paper and then washed with 300 ml of water. The still moist filter cake is recrystallised in 350 ml of boiling dimethylformamide for 17 hours (at first distilling off solvent/water mixture until the boiling temperature is 135° C.). The reaction product is filtered over a hard filter paper, washed with 130 ml of dimethylformamide, then with 150 ml of methanol and finally with 200 ml of water and is then dried, giving 5.7 g (46%) of an orange powder of formula (V), the isomeric compound of formula (VI)

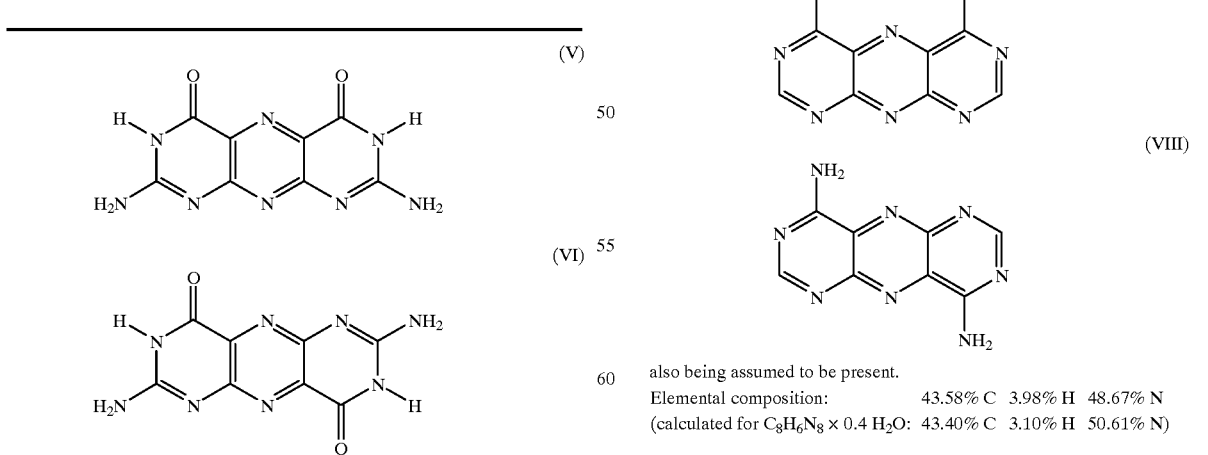

also being assumed to be present

| Elemental compostion: | 37.45% C | 3.29% H | 43.44% N |
|---|---|---|---|
| (calculated for $C_8H_6N_8O_2$ × 0.6$H_2O$: | 37.38% C | 2.82% H | 43.60% N) |

EXAMPLE 4

25.31 g of commercial 97% 4,5,6-triaminopyrimidinesulfate are made into a slurry in 300 ml of deionised water and 16.5 ml of 30% sodium hydroxide solution are added. This mixture is heated to 55° C. over 10 min and a moderate stream of air is introduced below surface. The temperature is raised to 80° C. over another 10 min. The mixture is stirred for a total of 22 hours at 80° C. with a constant stream of air, another 5.5 ml of 30% sodium hydroxide solution being added after one hour (on reaching the temperature of 80° C.). The yellowish orange suspension is then filtered hot over a hard filter paper and the filter cake is washed with 200 ml of water. The still moist filter cake is made into a slurry in 140 ml of 1 N sodium hydroxide solution and stirred for one hour at 90° C. The reaction mixture is filtered over a hard filter paper and the filter cake is washed with 100 ml of water until neutral. The moist filter cake is stirred in 140 ml of glacial acetic acid and recrystallised for one hour at 105° C. The reaction product is filtered over a hard filter paper, washed with 100 ml of water and then dried, giving 2.00 g (17%) of a yellow powder of formula (VII), the isomeric compound of formula (VIII)

also being assumed to be present.

| Elemental composition: | 43.58% C | 3.98% H | 48.67% N |
|---|---|---|---|
| (calculated for $C_8H_6N_8$ × 0.4 $H_2O$: | 43.40% C | 3.10% H | 50.61% N) |

EXAMPLE 5

13.23 g of commercial 90% 2,4,5,6-tetraaminopyrimidinesulfate are stirred at room temperature in 180 ml of water. 12.14 g of commercial 97% alloxane-tetrahydrate are added to this suspension, the colour of the reaction mixture changing from pale yellow to yellowish orange. The pH is then momentarily raised from about 0.5 to 6.5 by addition of 30% sodium hydroxide solution and the orange suspension is heated to 85° C. and stirred for 18 hours at this temperature. The suspension is allowed to cool to room temperature and is then filtered over a hard filter paper and the filter cake is washed with 500 ml of water. The still moist filter cake is made into a slurry in 500 ml of water and stirred for 4 hours at 90° C. The reaction mixture is filtered hot over a hard filter paper and and the residue is washed with 500 ml of water. The still moist residue is then recrystallised in 350 ml of dimethylformamide for 18 hours at 130° C. (at first distilling off solvent/water mixture). The reaction product is filtered over a hard filter paper, washed with 150 ml of dimethylformamide and 200 ml of methanol and dried, giving 9.1 g (74% of theory) of a yellowish orange powder of formula (IX)

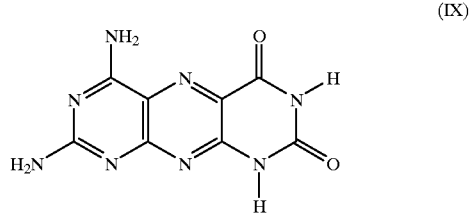

(IX)

Elemental composition: 37.75% C 3.38% H 41.64% N
(calculated for $C_8H_6N_8O_2 \times 1.25\ H_2O$: 35.76% C 3.19% H 41.70% N)

EXAMPLE 6

12.33 g of commercial 97% 6-hydroxy-2,4,5-triaminopyrimidinesulfate and 16.55 g of commercial 97% alloxanetetrahydrate are stirred in 300 ml of water at room temperature. The violet suspension is heated to 90° C. and stirred for 17 hours at this temperature reaction mixture, now yellow, is filtered over a hard filter paper and and the filter cake is washed with 450 ml of water. The still moist filter cake is stirred in 300 ml of dimethylformamide and recrystallised for 6 hours at 130° C. (at first distilling off solvent/water mixture). The reaction product is filtered over a hard filter paper and washed with 200 ml of methanol, then with 200 ml of water and is then dried, giving 8.37 g (63% of theory) of a yellow powder of formula (X)

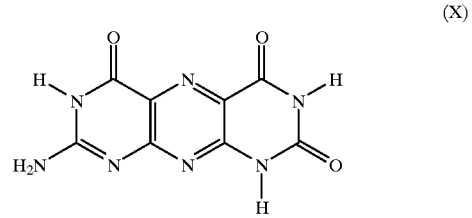

(X)

Elemental composition: 34.71% C 2.91% H 35.72% N
(calculated for $C_8H_5N_7O_3 \times 1.6\ H_2O$: 34.81% C 2.99% H 35.52% N)

EXAMPLES 7–12
Colorations in HDPE (high density polyethylene).
The General procedure is as follows:
A mixture consisting of 1.0 g of pigment, 1.0 g of antioxidant (IRGANOX®1010, Ciba) and 1000 g of polyethylene HD granulate (VESTOLEN®60-16, Hüls) is premixed for 15 minutes in a glass flask on a roller gear table. Subsequently, the mixture is extruded in two passes on a single screw extruder and the resulting granulate is moulded to plates on an injection moulding machine (Allround Aarburg 200) at 220° C. and then post-moulded for 5 minutes at 180° C.

| Example No. | Compound of formula | of Example | Colour obtained | Fastnesses obtained |
|---|---|---|---|---|
| 7 | (III) | 1 | yellow | very good |
| 8 | (IV) | 2 | orange-red | very good |
| 9 | (V) | 3 | yellowish orange | good |
| 10 | (VII) | 4 | yellow | very good |
| 11 | (IX) | 5 | yellow | very good |
| 12 | (X) | 6 | yellow | good |

EXAMPLES 13–18
Colorations in PVC
The general procedure is as follows:
0.6 g of pigment is mixed with 67 g of polyvinyl chloride, 33 g of dioctyl phthalate, 2 g of dibutyltin dilaurate and 2 g of titanium dioxide and processed to a thin film on a roll mill for 15 minutes at 160° C.

| Example No. | Compound of formula | of Example | Color obtained | Fastnesses obtained |
|---|---|---|---|---|
| 13 | (III) | 1 | yellow | very good |
| 14 | (IV) | 2 | orange-red | very good |
| 15 | (V) | 3 | yellowish orange | very good |
| 16 | (VII) | 4 | yellow | very good |
| 17 | (IX) | 5 | yellow | very good |
| 18 | (X) | 6 | yellow | good |

EXAMPLES 19–24
Colorations in AM Varnish
The general procedure is as follows:
2 g of pigment and 48 g of stoving lacquer consisting of
56 g of alkyd resin ALKYDAL®310 (Bayer AG; 60% in xylene)
13 g of melamine resin CYMEL®327 (Cyanamid; 90% in butanol)
25 g of xylene
25 g of butanol
2.5 g of 1-methoxy-2-propanol and
1 g of silicone oil (1% in xylene)
are mixed by conventional methods. The resultant colour lake is drawn to a film on a glass plate. Before stoving in a circulating air oven (30 minutes at 120° C.) the coating is allowed to dry in the air for 30 minutes at an inclination of 25°.

| Example No. | Compound of formula | of Example | Color obtained | Fastnesses obtained |
|---|---|---|---|---|
| 19 | (III) | 1 | yellow | very good |
| 20 | (IV) | 2 | orange-red | very good |

-continued

| Example No. | Compound of formula | of Example | Color obtained | Fastnesses obtained |
|---|---|---|---|---|
| 21 | (V) | 3 | yellowish orange | good |
| 22 | (VII) | 4 | yellow | good |
| 23 | (IX) | 5 | yellow | good |
| 24 | (X) | 6 | yellow | very good |

What is claimed is:

1. A process for mass colouring high molecular weight organic material with pyrimidopteridines, which comprises incorporating a tinctorially effective amount of a pyrimidopteridine of formula I and/or II

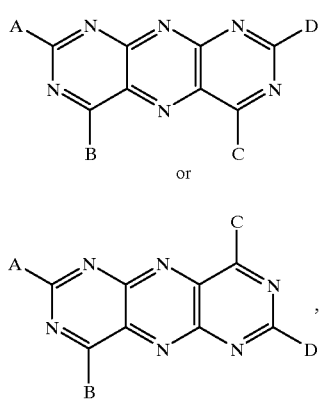

wherein A, B, C and D are each independently of one another —$NH_2$, —OH, hydrogen, $C_1$–$C_4$-alkyl; phenyl, biphenyl or naphthyl which are unsubstituted or substituted by halogen, —OH, —$NH_2$, $C_1$–$C_4$alkyl or $C_1$–$C_4$alkoxy; —$NHR_1$, —$N(R_1)_2$ or

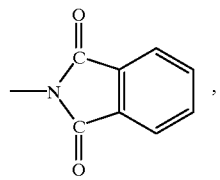

wherein $R_1$ is $C_1$–$C_4$alkyl; phenyl which is unsubstituted or substituted by halogen, $C_1$–$C_4$alkyl or $C_1$–$C_4$-alkoxy, or —$COXR_2$, X is a direct bond, —O— or —NH—, and $R_2$ is $C_1$–$C_4$alkyl; phenyl which is unsubstituted or substituted by halogen, $C_1$–$C_4$alkyl or $C_1$–$C_4$-alkoxy, with the proviso that at least two of the radicals A, B, C and D are —$NH_2$ or —OH, into the high molecular weight organic material.

2. A process according to claim 1, which comprises using pyrimidopteridines of formula I or II or a mixture thereof, wherein A, B, C and D are each independently of one another —$NH_2$, —OH, hydrogen, methyl, ethyl; phenyl which is unsubstituted or substituted by —OH or —$NH_2$, or —$NHCOXR_2$, wherein X is a direct bond, —O— or —NH—, and $R_2$ is $C_1$–$C_4$alkyl, or phenyl which is unsubstituted or substituted by chloro, methyl, ethyl, methoxy or ethoxy.

3. A process according to claim 1, which comprises using pyrimidopteridines of formula I or II or a mixture thereof, wherein A, B, C and D are each independently of one another —$NH_2$, —OH, hydrogen, methyl; phenyl which is unsubstituted or substituted by —$NH_2$, or $NHCOR_2$, and $R_2$ is methyl, ethyl or phenyl, wherein A and D are identical to one another and B and C are identical to one another and either A and D or B and C are —$NH_2$ or —OH.

4. A pyrimidopteridine of formulae I and/or II

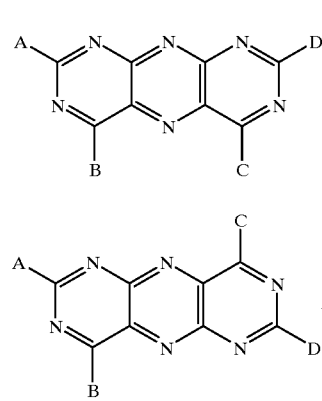

wherein A, B, C and D are each independently of one another —$NH_2$, —OH, hydrogen, $C_1$–$C_4$-alkyl; phenyl, biphenyl or naphthyl which are unsubstituted or substituted by halogen, —OH, —$NH_2$, $C_1$–$C_4$alkyl or $C_1$–$C_4$alkoxy; —$NHR_1$, —$N(R_1)_2$ or

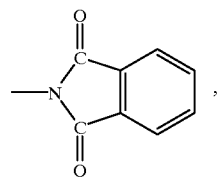

wherein $R_1$ is $C_1$–$C_4$alkyl; phenyl which is unsubstituted or substituted by halogen, $C_1$–$C_4$alkyl or $C_1$–$C_4$-alkoxy, or —$COXR_2$, X is a direct bond, —O— or —NH—, and $R_2$ is $C_1$–$C_4$alkyl; phenyl which is unsubstituted or substituted by halogen, $C_1$–$C_4$alkyl or $C_1$–$C_4$-alkoxy, with the proviso that at least two of the radicals A, B, C and D are —$NH_2$ or —OH, with the restriction that one or two of the radicals A, B, C or D are hydrogen, $C_1$–$C_4$alkyl; phenyl, biphenyl or naphthyl which are unsubstituted or substituted by halogen, —OH, —$NH_2$, $C_1$–$C_4$alkyl or $C_1$–$C_4$alkoxy; —$NHR_1$, —$N(R_1)_2$ or

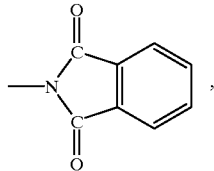

wherein $R_1$ is $C_1$–$C_4$alkyl; phenyl which is unsubstituted or substituted by halogen, $C_1$–$C_4$alkyl or $C_1$–$C_4$-alkoxy, or —$COXR_2$, X is a direct bond, —O— or —NH—, and $R_2$ is $C_1$–$C_4$alkyl; phenyl which is unsubstituted or substituted by halogen, $C_1$–$C_4$alkyl or $C_1$–$C_4$-alkoxy.

5. A pyrimidopteridine according to claim 4, wherein one or two of the radicals A, B, C or D are hydrogen, methyl, ethyl; phenyl which is unsubstituted or substituted by —OH or —$NH_2$, or —$NHCOXR_2$, wherein X is a direct bond, —O— or —NH—, and $R_2$ is $C_1$–$C_4$alkyl; phenyl which is unsubstituted or substituted by chloro, methyl, ethyl, methoxy or ethoxy.

6. A pyrimidopteridine according to claim 4, wherein a first pair A and D are identical to one another and a second pair B and C are identical to one another and the first pair is —OH or —$NH_2$ and the second pair is hydrogen, methyl; phenyl which is unsubstituted or substituted by —$NH_2$, or —$NHCOR_2$, and $R_2$ is methyl, ethyl or phenyl.

7. A composition comprising a high molecular weight organic material and a pyrimidopteridine of formula I and/or II

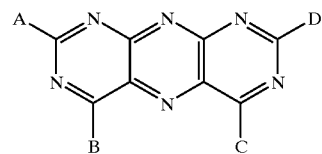

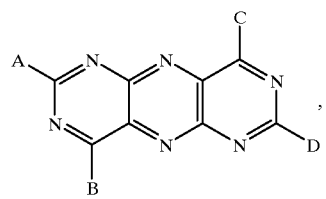

wherein A, B, C and D are each independently of one another —$NH_2$, —OH, hydrogen, $C_1$–$C_4$-alkyl; phenyl, biphenyl or naphthyl which are unsubstituted or substituted by halogen, —OH, —$NH_2$, $C_1$–$C_4$alkyl or $C_1$–$C_4$alkoxy; —$NHR_1$, —$N(R_1)_2$ or

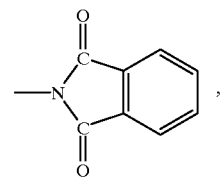

wherein
$R_1$ is $C_1$–$C_4$alkyl; phenyl which is unsubstituted or substituted by halogen, $C_1$–$C_4$alkyl or $C_1$–$C_4$-alkoxy, or —$COXR_2$,
X is a direct bond, —O— or —NH—, and
$R_2$ is $C_1$–$C_4$alkyl; phenyl which is unsubstituted or substituted by halogen, $C_1$–$C_4$alkyl or $C_1$–$C_4$-alkoxy, with the proviso that at least two of the radicals A, B, C and D are —$NH_2$ or —OH, or a mixture thereof.

8. A composition as claimed in claim 7, which comprises
(a) 0.05 to 20% by weight of pyrimidopteridines I and/or II, based on the sum of (a) and (b), and
(b) 99.95 to 80% by weight of a high molecular weight organic material, based on the sum of (a) and (b).

* * * * *